United States Patent
Wang et al.

(10) Patent No.: US 6,514,450 B1
(45) Date of Patent: Feb. 4, 2003

(54) METHOD AND APPARATUS FOR FORMING A CATHETER BALLOON

(75) Inventors: Chicheng Wang, Sunnyvale, CA (US); Eugene R. Serina, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/469,743

(22) Filed: Dec. 21, 1999

(51) Int. Cl.[7] .............................................. B29C 49/22
(52) U.S. Cl. ....................... 264/513; 264/138; 264/154; 264/155; 264/162
(58) Field of Search ................................ 264/513, 138, 264/154, 155, 162

(56) References Cited

U.S. PATENT DOCUMENTS

| | | | |
|---|---|---|---|
| 4,321,226 A | 3/1982 | Markling | 264/139 |
| 4,384,942 A | 5/1983 | Glowacki | 204/129.46 |
| 5,215,614 A | 6/1993 | Wijkamp et al. | 156/153 |
| 5,525,388 A | 6/1996 | Wand et al. | 428/36.9 |

*Primary Examiner*—Suzanne E. McDowell
(74) *Attorney, Agent, or Firm*—Fulwider Patton Lee & Utecht, LLP

(57) ABSTRACT

A method for medical balloon fabrication comprising the steps of securing a balloon with a mold by inflating it and then enlarging the inner diameter of the balloon. The devices of the invention comprise a fixture with a mold configured to hold the inflated balloon and a drill that can be centered with the mold to enlarge the inner diameter of the balloon.

8 Claims, 2 Drawing Sheets

METHOD AND APPARATUS FOR FORMING A CATHETER BALLOON

BACKGROUND OF THE INVENTION

This invention relates generally to the field of medical devices, and particularly to a method and apparatus for forming a catheter balloon in which balloon material is removed from an inner surface of the balloon.

Medical balloon catheters, particularly those configured for use in the peripheral vasculature anatomy, desirably have relatively large working balloon diameters coupled with relatively small diameter catheter shafts. Details of angioplasty and peripheral vasculature balloon catheter design can be found in U.S. Pat. Nos. 5,042,985 and 5,061,273, incorporated herein by reference in their entireties. A conventional technique for fabricating catheter balloons involves blow molding a parison. The parison, or balloon tubing, must have sufficient wall thickness to provide enough material to allow expansion of the parison to the working diameter of the balloon during the blow molding operation. Furthermore, the diameter of the parison must be compatible with the shaft diameter of the catheter to which the balloon will be attached. A parison is prepared, as for example by extruding tubing having wall thickness sufficient to provide material for blowing the balloon. Typically, the proximal and distal sections of the tubing are necked to reduce the diameter to be compatible with the desired catheter shaft, using a hot die and a mandrel. The outer diameter of the necked tube is controlled by the diameter of the die, while the native wall thickness of the tubing generally limits the size of the mandrel that may be used, and thus, the resulting inner diameter. Prior art techniques have difficulty generating satisfactory parisons for a relatively large diameter balloon configured for use with a relatively small diameter catheter shaft. The diameter of the proximal and distal portions of the parison is dictated by the diameter of the catheter shaft. When preparing parisons for a larger diameter balloon, the greater wall thickness required for blowing the balloon necessitates the use of a smaller mandrel. This can result in an undesirably small inner diameter in the proximal and distal portions of the parison that are not expanded or expanded very little during the blow molding operation.

Accordingly, there is a need for methods of forming balloons for catheters that couple a relatively large diameter balloon with a relatively small diameter catheter shaft. There is a further need for balloon forming methods that provide a relatively large diameter balloon with a relatively small diameter catheter shaft that still have sufficient inner diameters. Additionally, there is a need for such balloon fabrication techniques that are cost effective, improve reliability and are compatible with conventional blow molding methods. This invention satisfies these and other needs.

SUMMARY OF THE INVENTION

The invention is inflatable members for catheters, and a method of forming such inflatable members, generally comprising providing an inflatable member with a section having an inner diameter, and enlarging the inner diameter of the section of the inflatable member. In a presently preferred embodiment, the section to be enlarged is a generally noninflatable shaft section of the balloon. A presently preferred embodiment comprises placing at least a section of the inflatable member in a mold, inflating the section of the inflatable member to conform the inflatable member to the interior surface of the mold, and removing material from the inner surface of the inflatable member, such as for example, an inner surface of the proximal shaft section and/or distal shaft section of the inflatable member. Preferably, the step of enlarging the inner diameter of the shaft section of the inflatable member comprises removing material from the inner surface of the shaft section, as for example by abrading, machining or drilling. The balloon may be formed by a variety of suitable methods such as blow molding in a first balloon mold, and then put into a second mold of an assembly for removing material from the shaft section to thin the shaft section wall.

The invention also includes devices for enlarging the inner diameter of a section of an inflatable member, generally comprising a mold configured to cover at least a section of the inflatable member and a drill at one end of the mold. A presently preferred embodiment comprises a fixture secured to a mold, the mold having an inner dimension corresponding to the outer dimension of the inflated inflatable member, a drill centered axially with the mold, and a fitting for introducing pressurized air into the inflatable member. The mold may encompass the entire length or less than the entire length of the inflatable member. The pressurized air blows cutting debris away from the balloon, and displaces the central working length of the balloon radially away from the path of the drill, both of which would otherwise damage the balloon wall.

The method and apparatus of the invention provides a catheter balloon having an enlarged inner diameter shaft section, without damaging the balloon during enlargement of the shaft inner diameter, and may be used to prepare a balloon with a large working diameter and a desired shaft section diameter. These and other advantages will become more apparent from the following exemplary figures and detailed description.

DETAILED DESCRIPTION OF THE INVENTION

Figure 1:
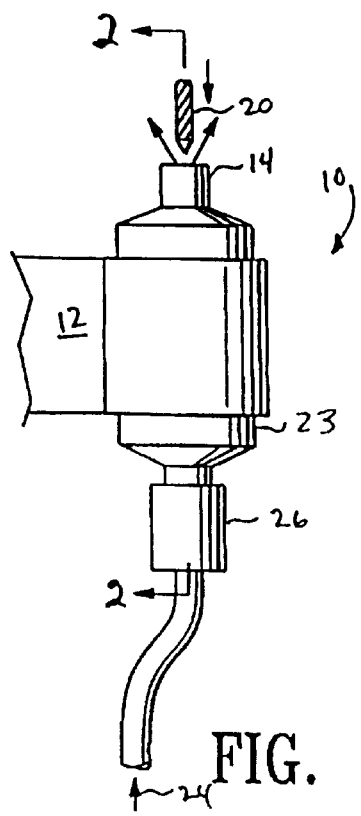
FIG. 1 is an elevational view of a balloon drilling apparatus which embodies features of the invention, and which is useful in the practice of the invention.
Figure 2:
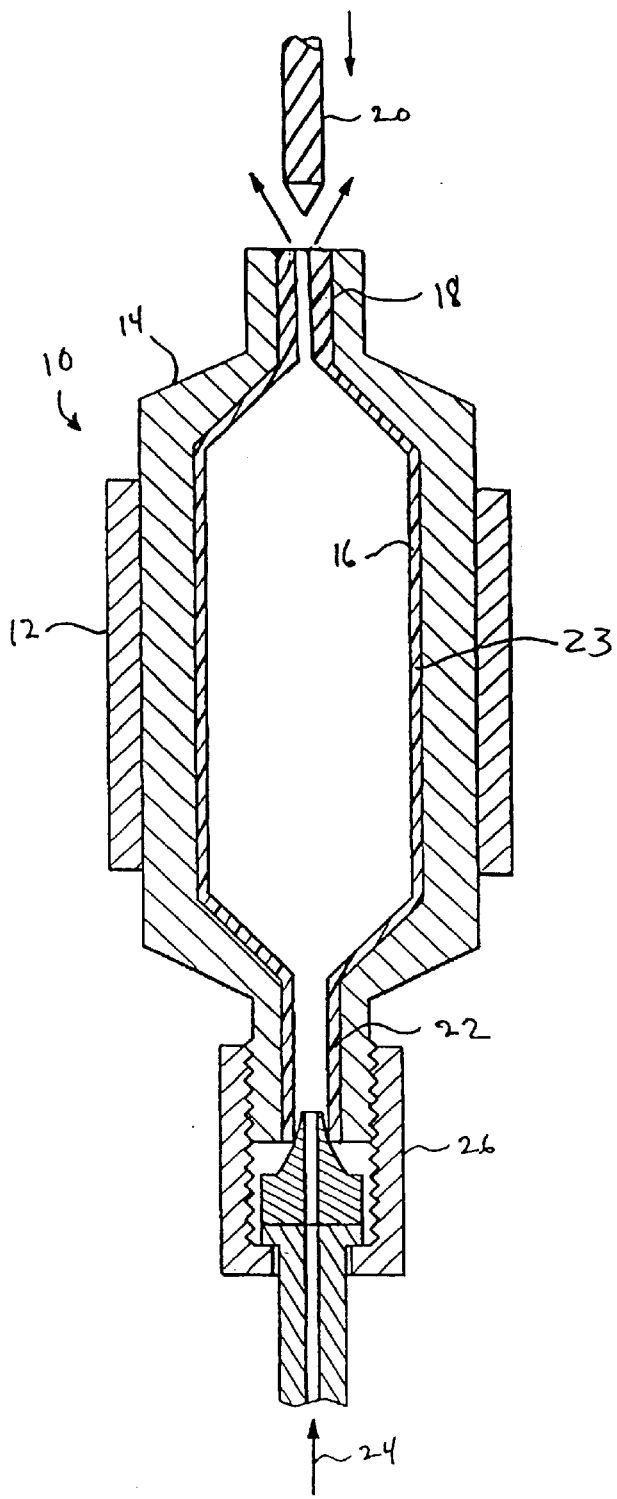
FIG. 2 is a longitudinal cross-sectional. View of the apparatus shown in FIG. 1.

In the embodiment illustrated schematically in FIG. 1 and in section in FIG. 2, an apparatus 10 useful in the practice of this invention generally comprises a fixture 12 secured to a mold 14, the mold having inner dimensions equal to the desired outer dimensions of the inflated inflatable member 16. The inflatable member has a proximal shaft section 18, a distal shaft section 22, and a central, working section 23 therebetween. An inflatable member 16, which has been formed, as for example by.blow molding a parison, is placed within the mold 14, and a pressurized fluid such as air is supplied to the interior of the inflatable member to inflate the inflatable member and secure it within the mold. Fixture presents proximal section 18 of inflatable member 16 to inflatable member material removal member 20. In the embodiment illustrated in FIG. 1, the inflatable member material removal member 20 is a drill. Once inflatable member 16 is placed within the mold and inflated to secure it, drill 20 is used to increase the inner diameter of the proximal section 18. Inflatable member 16 can be deflated, turned end for end, and then reinflated to allow drilling of distal section 22, or vise versa. In a presently preferred embodiment, the inflatable member inner diameter is drilled at room temperature (25° C.) or below room temperature, as for example by cooling the balloon to about 20° C. to about −20° C. Preferably, a drill press (not shown) is secured to fixture 12 so that drill 20 may be aligned axially with the center of mold 14, and likewise the center of the inflatable member 16. Further, fixture 12 should be designed to accommodate molds 14 of varying dimensions. Typically, the wall thickness of the balloon proximal section or distal section is reduced by about 10% to about 70%, and preferably about 10% to about 50%, and the inner diameter is increased by about 10% to about 150% during the enlarging operation. For a given balloon, the preferred percent reduction in the wall thickness of the balloon proximal or distal shaft sections will depend on the outer diameter of the balloon, i.e., larger balloon having a working section with an inflated outer diameter of about 6 mm to 10 mm preferably have the proximal or distal shaft sections reduced by about 10% to about 60%, preferably about 50%, and smaller balloons having an outer diameter of about 4 mm to about 5 mm preferably have the proximal or distal shaft sections reduced by about 50% to about 70%.

In the embodiment illustrated in FIG. 2, the distal section 22 of the balloon has been enlarged using the method of the invention, and the proximal section 18 is in the process of being enlarged before the drill 20 is positioned within the end of the mold into contact with the inner surface of the proximal section 18.

Pressurized air 24 is supplied to inflatable member 16 via fitting 26, and generally should be regulated. Sufficient pressure should be used to hold the inflatable member 16 tightly in mold 14, thus resisting rotational and axial movement when the drill is advanced. The air pressure is about 2 psi to about 250 psi, and is sufficient to inflate the balloon and blow cutting debris away from the drilling operation to prevent debris from falling into inflatable member 16. By inflating inflatable tubular member 16 against mold 14, the air pressure also ensures that the balloon walls are kept out of the path of drill 20, preventing damage.

In the presently preferred method illustrated in FIG. 1, the balloon 16 is within a mold 14 which extends the length of the balloon during enlargement of the inner diameter of the balloon shaft section. Alternatively, a section of the balloon may be within a mold having a length less than the length of the balloon.

An inflatable member formed using the method of the invention generally has proximal section 18 configured to be secured to a first catheter shaft section such as an outer tubular member of the catheter shaft, and distal section 22 configured to be secured to a second catheter shaft section such as an inner tubular member of the catheter shaft. In the method of the invention, the inner diameter of the proximal section and/or distal section of the balloon can be enlarged to a desired dimension prior to being secured to the catheter shaft. The proximal section 18 of the balloon generally has an outer diameter of about 0.8 mm to about 2.0 mm, and an inner diameter, before being enlarged, of about 0.5 mm to about 1.5 mm. Using the method of the invention, the inner diameter of the proximal section 18 is generally enlarged to about 1.0 mm to about 1.7 mm, so that the proximal section wall thickness is reduced to about 0.2 mm to about 0.7 mm. The distal section 22 of the balloon generally has an outer diameter of about 0.8 mm to about 2.0 mm, and an inner diameter, before being enlarged, of about 0.5 mm to about 1.5 mm. Using the method of the invention, the inner diameter of the distal section 22 is generally enlarged to about 1.0 mm to about 1.7 mm, so that the distal section wall thickness is reduced to about 0.8 mm to about 2.0 mm.

The drilling operation should be tailored to the nature of the polymeric material being removed. For example, if shear heating or deformation of the material is problematic, it may be desirable to use sequentially larger diameter drill bits to increase the inner diameter of proximal and distal sections 18 and 22 gradually. Drill bits suitable for use in the method of the invention have diameters of generally about 1.0 mm to about 1.7 mm. The rotational speed is typically about 5 rpm to about 1000 rpm, and typically about 100 rpm to about 500 rpm depending on the type of material used to form the balloon, and the rate of advance is typically about 1 mm/sec to about 10 mm/sec, and may be varied to optimize the operation. It may also be desirable to use a drill bit configured for the relatively soft polymeric materials, such as a wood drill or a multiple-flute end mill. Further, it may be desirable to provide drill 20 with upcutting flutes to direct the cutting debris out of inflatable member 16. Although drill 20 is particularly suited to the invention, other suitable inflatable member material removers may be employed, including scrapers, blades, lasers, and grinders.

Figure 3:
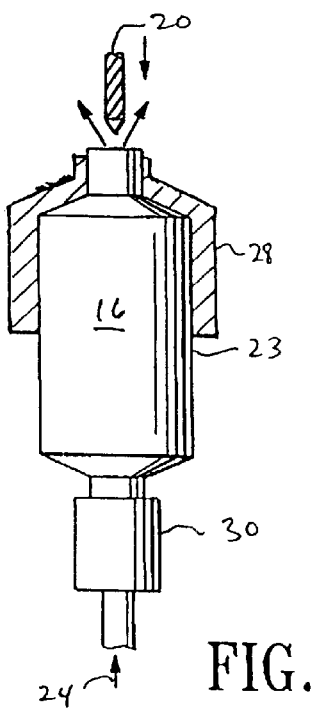
FIG. 3 is an elevational view, partially in section, of an alternate embodiment of a balloon drilling apparatus which embodies features of the invention, and which is useful in the practice of this invention.
Figures 4, 5:
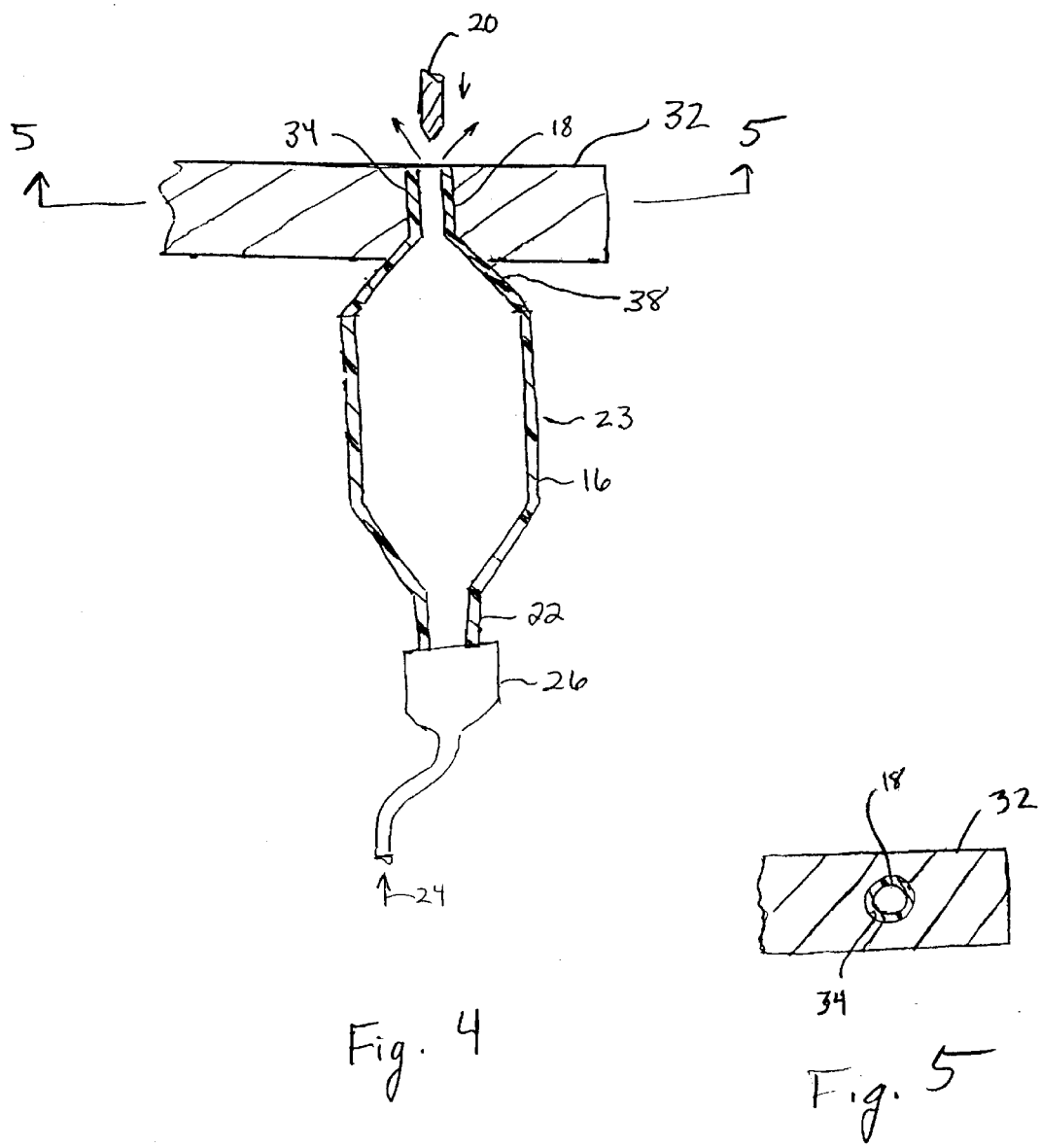
FIG. 4 is an elevational view, partially in longitudinal cross section, of an embodiment embodying features of the invention having a mold with a length less than the length of the balloon.
FIG. 5 is a transverse cross sectional view of the mold illustrated in FIG. 4, taken along lines 5—5.

In the embodiment shown in FIGS. 1 and 2, mold 14 encompasses the overall dimensions of inflatable member 16. However, in alternative embodiments illustrated in FIGS. 3 and 4, a mold is used which encompasses only a portion of the balloon, and which can accommodate inflatable members having varying working lengths. The mold may also be designed to accommodate inflatable members having varying diameters. In the embodiment illustrated in FIG. 3, mold 28 is configured to receive a portion of the working section 23 of the balloon 16, and provides sufficient contact area between mold 28 and inflatable member 16 to adequately secure inflatable member 16 during the drilling operation. In a presently preferred embodiment, the mold 28 contacts about 5% to about 95% of the working section 23 of the inflatable member. In this embodiment, fitting 30 for delivering pressurized air to the inflatable member is configured to attach directly to inflatable member 16. In the embodiment illustrated in FIG. 4, mold 32 has an interior chamber 34 configured to receive at least balloon shaft section 18 or 22 therein, but the working length 23 of the balloon 16 is not within mold 32 during enlargement of the balloon shaft section inner diameter. In the embodiment illustrated in FIG. 4, the mold chamber 34 is configured to receive a section of the balloon tapered section 38. FIG. 5 illustrates a transverse cross section of the mold 32 shown in FIG. 4 taken along lines 5—5. When the mold has a length less than the length of the balloon so that it is configured to contain the balloon shaft section and not the entire length of the balloon, the air pressure used during the enlargement to inflate the balloon and blow cutting debris away is about 2 to about 150 psi, preferably about 80 to about 100 psi.

A balloon configured for use in an over-the-wire type carotid artery catheter can be made using the method and apparatus of the invention which will have a working diameter of at least about 6.0 mm (nominal), mounted on a catheter having a catheter shaft having an outer diameter at the location of the connection with the proximal balloon shaft section 18 of about 0.055 inch to about 0.060 inch, and an outer diameter at the location of the connection with the distal balloon shaft section 22 of about 0.045 inch to about 0.050 inch, so that the catheter is sized for use with a guidewire having an outer diameter of about 0.014 inch to about 0.018 inch. Before the inner diameter is enlarged according to the method of the invention, the proximal shaft section 18 of the balloon 22 has an inner diameter of about 0.012 inch and the wall thickness of about 0.016 inch, and the distal shaft section 22 of the balloon 16 has an inner diameter of about 0.007 inch and a wall thickness of about 0.013 inch. After the inner diameter is enlarged according to the method of the invention, the proximal shaft section 18 of the balloon will have has an inner diameter of about 0.8 mm to about 1.0 mm, preferably about 0.94 mm, and an outer diameter of about 0.9 mm to 1.2 mm, preferably about 1.1 mm and the distal shaft section 22 of the balloon will have and inner diameter of about 0.4 mm to about 0.6 mm, preferably about 0.56 mm, and an outer diameter of about 0.7 mm to about 0.9 mm, preferably about 0.86 mm. Using the prior art methods of forming a catheter balloon, although tubing having the correct wall thickness to blow a 6.0 mm diameter balloon can be necked to the required outer diameter for blowing the balloon and joining the balloon to the catheter shaft, the resulting inner diameter is not suitable. Despite multiple attempts using different die temperatures, and using a die having the maximum permissible diameter, the largest diameter mandrel that could be used was 0.007 inches (0.18 mm). This results in an unacceptably small inner diameter in the proximal and distal sections of the parison. Accordingly, it is necessary to increase the inner diameter of the balloon using the methods and devices of this invention. Other prior art balloons with a working length having a 6.0 mm outer diameter and balloon shaft sections having a relatively thin wall thickness of about 0.007 inch were typically mounted on catheter shafts having a relatively large inner diameter (of about 0.047 inch) and a relatively large outer diameter (of about 0.054 inch). In contrast, the balloon of the invention has shaft sections having a relatively small outer diameter and wall thickness, and configured to be mounted on a catheter shaft having a relatively small outer diameter compared to prior art balloons.

While the present. Invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method for inflatable member fabrication, comprising:
    a) placing inside a mold at least a portion of an inflatable member having a first section with an inner diameter, a second section with an inner diameter, and a third section located between the first and second sections; and
    b) supplying pressurized fluid to an interior of the inflatable member to inflate the inflatable member and conform said portion of the inflatable member to an interior surface of the mold; and
    c) removing material from the first section to enlarge the inner diameter of the first section of the inflatable member.

2. The method of claim 1, including cooling at least the first section to below room temperature after step a) in claim 1.

3. The method of claim 1, further comprising enlarging the inner diameter of the second section of the inflatable member by removing material therefrom.

4. The method of claim 1, wherein material is removed from the first section by drilling.

5. The method of claim 4, wherein enlarging the inner diameter of the first section comprises sequentially drilling with increasing diameter drill bits.

6. The method of claim 4, wherein the fluid is pressurized gas, and further including directing the gas from the second section to the first section, to remove. material cuttings from inside the inflatable member that are formed by the drilling by blowing the cuttings in a direction opposite to a direction of the drilling.

7. The method of claim 1 wherein said portion includes part of a working length of the inflatable member.

8. The method of claim 1, further comprising forming the inflatable member by necking tubing having proximal and distal sections and blow molding the necked tubing prior to step a).

* * * * *

UNITED STATES PATENT AND TRADEMARK OFFICE
CERTIFICATE OF CORRECTION

PATENT NO. : 6,514,450 B1
DATED : February 4, 2003
INVENTOR(S) : Chicheng Wang et al.

It is certified that error appears in the above-identified patent and that said Letters Patent is hereby corrected as shown below:

Column 6,
Line 36, after "remove", delete ".".

Signed and Sealed this

Tenth Day of June, 2003

JAMES E. ROGAN
*Director of the United States Patent and Trademark Office*